United States Patent
Kai et al.

(10) Patent No.: US 9,133,205 B2
(45) Date of Patent: Sep. 15, 2015

(54) ORGANIC ELECTROLUMINESCENT DEVICE

(75) Inventors: Takahiro Kai, Kitakyushu (JP); Masaki Komori, Kitakyushu (JP); Toshihiro Yamamoto, Kitakyushu (JP); Megumi Matsumoto, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 507 days.

(21) Appl. No.: 13/578,207

(22) PCT Filed: Feb. 7, 2011

(86) PCT No.: PCT/JP2011/052532
§ 371 (c)(1),
(2), (4) Date: Aug. 9, 2012

(87) PCT Pub. No.: WO2011/099451
PCT Pub. Date: Aug. 18, 2011

(65) Prior Publication Data
US 2012/0305904 A1  Dec. 6, 2012

(30) Foreign Application Priority Data
Feb. 12, 2010  (JP) ................. 2010-028569

(51) Int. Cl.
*H01L 51/54* (2006.01)
*C09K 11/06* (2006.01)
*C07D 487/14* (2006.01)
*C07D 519/00* (2006.01)
*H01L 51/00* (2006.01)
*H05B 33/10* (2006.01)
*H01L 51/50* (2006.01)

(52) U.S. Cl.
CPC ............ *C07D 487/14* (2013.01); *C07D 519/00* (2013.01); *C09K 11/06* (2013.01); *H01L 51/0072* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *H01L 51/0085* (2013.01); *H01L 51/5012* (2013.01)

(58) Field of Classification Search
None
See application file for complete search history.

(56) References Cited

U.S. PATENT DOCUMENTS

| | | | |
|---|---|---|---|
| 5,942,340 A | 8/1999 | Hu et al. | |
| 7,402,681 B2 | 7/2008 | Ong et al. | |
| 8,062,769 B2 | 11/2011 | Kai et al. | |
| 2002/0034655 A1 | 3/2002 | Watanabe et al. | |
| 2006/0063037 A1 | 3/2006 | Kim et al. | |
| 2008/0220285 A1* | 9/2008 | Vestweber et al. | 428/690 |
| 2011/0062429 A1 | 3/2011 | Kai et al. | |

FOREIGN PATENT DOCUMENTS

| | | |
|---|---|---|
| JP | 2007-288034 A | 11/2007 |
| WO | WO-01/41512 A1 | 6/2001 |
| WO | WO-2009/148015 A1 | 12/2009 |

OTHER PUBLICATIONS

International Search Report for the Application No. PCT/JP2011/052532 mailed Mar. 29, 2011.
International Preliminary Report on Patentability for the Application No. PCT/JP2011/052532 mailed Sep. 27, 2012.

* cited by examiner

Primary Examiner — Andrew K Bohaty
(74) Attorney, Agent, or Firm — Cheng Law Group, PLLC

(57) ABSTRACT

Disclosed is an organic electroluminescent device (organic EL device) that is improved in luminous efficiency, sufficiently secures driving stability, and has a simple configuration. This organic EL device has a light-emitting layer between an anode and a cathode piled one upon another on a substrate and the said light-emitting layer contains a fused polycyclic compound in which seven or more rings are fused together as a host material. The aforementioned fused polycyclic compound has a structure formed by fusing two or more indole rings to a carbazole ring. A specific example thereof is the compound represented by the following formula.

5 Claims, 1 Drawing Sheet

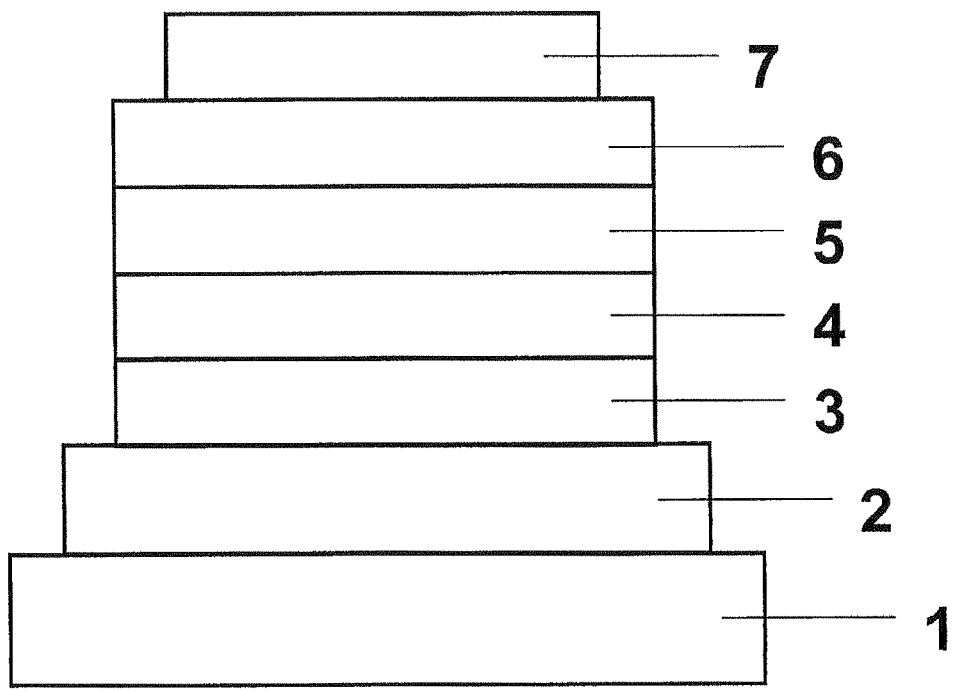

ORGANIC ELECTROLUMINESCENT DEVICE

TECHNICAL FIELD

This invention relates to an organic electroluminescent device containing an indolocarbazole compound and, more particularly, to a thin film type device that emits light upon application of an electric field to a light-emitting layer composed of an organic compound.

BACKGROUND TECHNOLOGY

An organic electroluminescent device (hereinafter referred to as organic EL device) in the simplest structure is generally constituted of a light-emitting layer and a pair of counter electrodes holding the light-emitting layer between them. The organic EL device functions by utilizing the following phenomenon; upon application of an electric field between the electrodes, electrons are injected from the cathode and holes are injected from the anode and they recombine in the light-emitting layer with emission of light.

In recent years, studies have been started to develop organic EL devices in which organic thin films are used. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been directed toward practical applications to high-performance flat panels featuring self-luminescence and high-speed response.

Further, in an effort to enhance the luminous efficiency of the device, the use of phosphorescence in place of fluorescence is investigated. The aforementioned device comprising a hole-transporting layer composed of an aromatic diamine and a light-emitting layer composed of Alq3 and many others have utilized fluorescence. However, the utilization of phosphorescence, that is, emission of light from the triplet excited state, is expected to enhance the luminous efficiency three to four times that of the conventional devices utilizing fluorescence (emission of light from the singlet excited state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they too failed to emit light at high efficiency. In recent years, as stated in patent document 1, a large number of researches are conducted on phosphorescent dopant materials, with a focus on the use of organic metal complexes such as iridium complexes, for the purpose of enhancing the luminous efficiency and extending the life.

PRIOR ART TECHNICAL DOCUMENTS

Patent Documents

Patent document 1: JP 2003-515897 A
Patent document 2: JP 2001-313178 A
Patent document 3: JP 4388590
Patent document 4: WO 2009-148015
Patent document 5: JP 2006-193729 A In order to obtain high luminous efficiency, a host material to be used together with the aforementioned dopant material becomes important. Of the host materials proposed thus far, a typical example is 4,4'-bis(9-carbazolyl)biphenyl (hereinafter referred to as CBP) presented in patent document 2. Since CBP is characterized by having a good hole transfer property but a poor electron transfer property, the use of CBP as a host material for tris(2-phenylpyridine)iridium complex (hereinafter referred to as Ir(ppy)$_3$), a typical phosphorescent green light-emitting material, disturbs the balanced injection of charges and causes excessive holes to flow out to the side of the electron-transporting layer. The result is a reduction in the luminous efficiency of Ir(ppy)$_3$.

In order for an organic EL device to display high luminous efficiency, a host material that has high triplet excitation energy and is well balanced in the injection and transportation characteristics of electric charges (holes and electrons) is required. Furthermore, compounds that are electrochemically stable, highly resistant to heat, and excellently stable in the amorphous state are desired and further improvements are demanded.

Patent document 3 discloses the compound illustrated below as a host material.

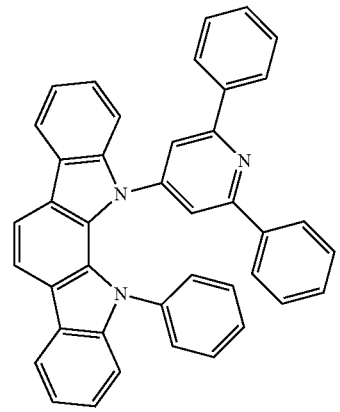 [SMILES: c1ccc(-c2cc(-n3c4ccccc4c4ccc5c6ccccc6n(-c6ccccc6)c5c43)cc(-c3ccccc3)n2)cc1]

However, the said document only describes the use of a compound having an indolocarbazole skeleton and a nitrogen-containing heterocyclic ring in the molecule and by no means discloses a compound having a skeleton formed by fusing together alternately five-membered nitrogen-containing rings and six-membered aromatic hydrocarbon rings in a combined total of 7 rings or more.

Patent document 4 discloses the compound illustrated below as a host material.

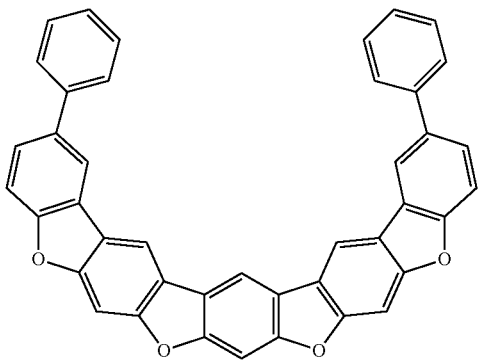 [SMILES: c1ccc(-c2ccc3oc4cc5oc6cc7oc8cc9oc%10ccc(-c%11ccccc%11)cc%10c9cc8c7cc6c5cc4c3c2)cc1]

The said document discloses a compound in which five-membered chalcogen-containing rings and six-membered aromatic hydrocarbon rings are alternately fused together. However, the document does not concretely disclose a compound in which five-membered nitrogen-containing rings and six-membered aromatic hydrocarbon rings are alternately fused together in a combined total of 7 rings or more and by no means discloses the usefulness of such a compound.

Further, patent document 5 discloses the compound illustrated below.

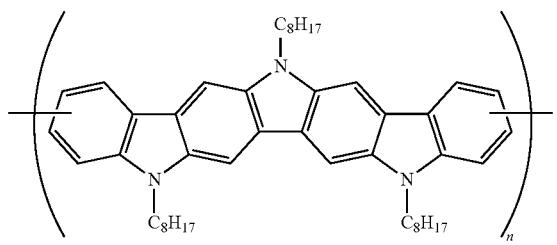

However, the document discloses only the use of the compound illustrated above in thin film transistors and by no means discloses the use in organic EL devices.

Disclosure of the Invention

In applications of organic EL devices to display devices such as flat panel displays, it is necessary to enhance the luminous efficiency of the device and, at the same time, to sufficiently secure the driving stability of the device. Under the aforementioned circumstances, an object of this invention is to provide an organic EL device exhibiting such luminous efficiency and driving stability as to be practically useful and to provide a compound suitable therefor.

The inventors of this invention have conducted intensive studies, found that the use of an indolocarbazole compound composed of nitrogen-containing aromatic heterocyclic rings and aromatic hydrocarbon linking groups in an organic EL device enables the device to display excellent characteristics, and completed this invention.

This invention relates to an organic electroluminescent device comprising an anode, organic layers containing a phosphorescent light-emitting layer, and a cathode piled one upon another on a substrate wherein at least one organic layer selected from the group consisting of a light-emitting layer, a hole-transporting layer, an electron-transporting layer, a hole-blocking layer, and an electron-blocking layer contains a compound represented by general formula (1).

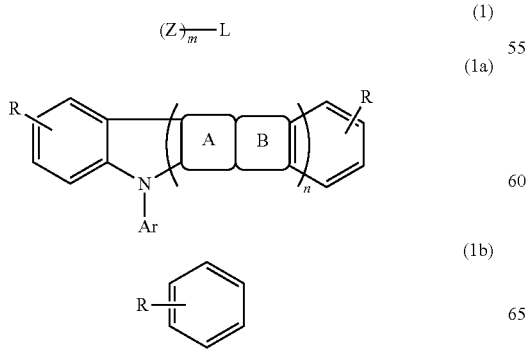

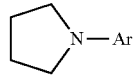

In general formula (1), Z is a group formed from a compound represented by formula (1a) by removing one of Ars possessed by the said compound; L is an aromatic hydrocarbon group of 6 to 50 carbon atoms or an aromatic heterocyclic group of 3 to 50 carbon atoms; m is an integer of 1 to 4 and, when m is 2 or more, Zs may be identical with or different from one another.

In formula (1a), ring A is a hydrocarbon ring represented by formula (1b) and fused to the adjacent rings at arbitrary positions, ring B is a heterocyclic ring represented by formula (1c) and fused to the adjacent rings at arbitrary positions, and n is an integer of 2 to 4. In formulas (1a) and (1b), each of a plurality of Rs is independently a hydrogen atom, an aliphatic hydrocarbon group of 1 to 10 carbon atoms, an aromatic hydrocarbon group of 6 to 18 carbon atoms, or an aromatic heterocyclic group of 3 to 17 carbon atoms. In formulas (1a) and (1c), each of a plurality of Ars is independently an aromatic hydrocarbon group of 6 to 50 carbon atoms or an aromatic heterocyclic group of 3 to 50 carbon atoms; however, at least one of L and a plurality of Ars is an m-valent or monovalent group formed from a compound represented by formula (1d) by removing hydrogen atoms or a hydrogen atom.

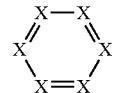

In formula (1d), X is a methine group, a nitrogen atom, or C—$Ar_1$ and at least one of Xs is a nitrogen atom; each $Ar_1$ is independently an aromatic hydrocarbon group of 6 to 50 carbon atoms or an aromatic heterocyclic group of 3 to 50 carbon atoms.

In general formula (1), m is preferably 1 or 2. Moreover, in formula (1a), n is preferably 2.

Further, formula (1a) is preferably represented by any one of formulas (2) to (4) shown below.

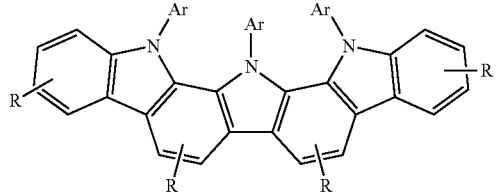

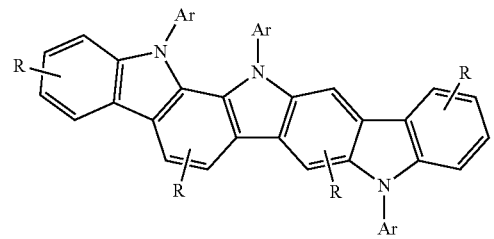

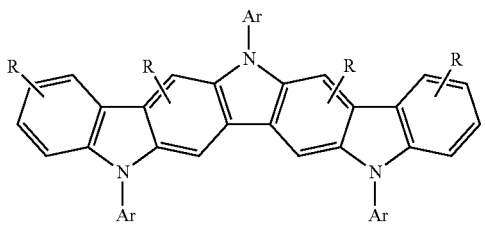
(4)

In formulas (2) to (4), Ar and R respectively have the same meaning as those in formulas (1a), (1b), and (1c).

It is preferable that, in the organic electroluminescent device of this invention, the organic layer containing the aforementioned compound is a light-emitting layer containing a phosphorescent dopant.

A compound represented by general formula (1) has a configuration in which five-membered nitrogen-containing rings and six-membered aromatic hydrocarbon rings are alternately fused together in a combined total of 7 rings or more. It is conceivable that the use of this compound in an organic EL device enables the device to display good injection and transportation characteristics of holes and electrons and have high durability. An organic EL device using this compound functions at low driving voltage. Particularly, in the case where the compound is incorporated in the light-emitting layer, the balance of electric charges in the device improves and, as a result, the probability of recombination improves. Furthermore, the compound has high energy in the lowest excited triplet state and can suppress transfer of the triplet excitation energy from the dopant to the host molecule and this characteristic is likely to provide excellent luminous characteristics. In addition, the compound exhibits a good property in the amorphous state and high thermal stability and is electrochemically stable and these properties conceivably contribute to realize organic EL devices of long driving life and high durability.

BRIEF DESCRIPTION OF THE DRAWINGS

FIG. 1 shows an example of the structure of an organic EL device.

PREFERRED EMBODIMENTS OF THE INVENTION

An organic electroluminescent device according to this invention contains a compound represented by the aforementioned general formula (1). That is, as shown by formula (1a), the compound has a skeleton formed by additionally fusing 1 to 3 indole rings in series to the indolocarbazole ring. Further, the compound has at least one non-fused nitrogen-containing heterocyclic ring on a nitrogen atom in the aforementioned skeleton.

In general formula (1), L is an m-valent aromatic hydrocarbon group of 6 to 50 carbon atoms or an m-valent aromatic heterocyclic group of 3 to 50 carbon atoms; preferably an m-valent aromatic hydrocarbon group of 6 to 18 carbon atoms or an m-valent aromatic heterocyclic group of 3 to 18 carbon atoms.

Specific examples of the aromatic hydrocarbon group and the aromatic heterocyclic group include groups formed by removing a hydrogen atom or hydrogen atoms from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, ovalene, corannulene, fulminene, anthanthrene, zethrene, terrylene, naphthacenonaphthacene, truxene, furan, benzofuran, isobenzofuran, xanthene, oxanthrene, dibenzofuran, perixanthenoxanthene, thiophene, thioxanthene, thianthrene, phenoxathiine, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, indolocarbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, thebenidine, quindoline, quinindoline, acrindoline, phthaloperine, triphenodithiazine, triphenodioxazine, phenanthrazine, anthrazine, benzothiazole, benzimidazole, benzoxazole, benzisoxazole, and benzoisothiazole or from aromatic compounds in which a plurality of these aromatic rings are linked together. Preferred are groups formed by removing a hydrogen atom or hydrogen atoms from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, and indolocarbazole or from aromatic compounds in which these aromatic rings are linked together. In the case where the groups are formed from the aromatic compounds in which a plurality of aromatic rings are linked together, the number of linked aromatic rings is preferably 2 to 10, more preferably 2 to 7, and the aromatic rings to be linked may be identical with or different from one another. In this case, the position of linkage of L to N in the ring represented by formula (1a) is not limited and the linkage may occur in the ring at the end or in the middle of the linked rings. The "aromatic ring" here is used as a general term to cover both the aromatic hydrocarbon ring and the aromatic heterocyclic ring.

In the case where the groups derived from the aromatic compounds in which a plurality of aromatic rings are linked together are divalent, such divalent groups are represented, for example, by the following general formulas (11) to (13);

 (11)

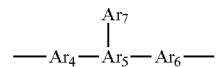 (12)

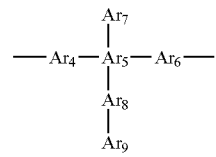 (13)

(In formulas (11) to (13), each of $Ar_4$ to $Ar_9$ is a substituted or unsubstituted aromatic ring.)

Specific examples of the aforementioned groups formed from the aromatic compounds in which a plurality of aromatic rings are linked together include groups formed by removing a hydrogen atom or hydrogen atoms from biphenyl, terphenyl, bipyridine, bipyrimidine, bitriazine, terpyridine, bistriazylbenzene, dicarbazolylbenzene, carbazolylbiphenyl, dicarbazolylbiphenyl, indolocarbazolyltriazine, phenylterphenyl, carbazolylterphenyl, binaphthalene, phenylpyridine, phenylcarbazole, diphenylcarbazole, diphenylpyridine, phenylpyrimidine, diphenylpyrimidine, phenyltriazine, diphenyltriazine, phenylnaphthalene, diphenylnaphthalene, indolocarbazolylbenzene, indolocarbazolylpyridine, and indolocarbazolyltriazine.

The aforementioned aromatic rings may have a substituent. In the case where the aromatic rings have a substituent, preferable examples of the substituent include an alkyl group of 1 to 4 carbon atoms, a cycloalkyl group of 3 to 6 carbon atoms, an alkoxyl group of 1 to 2 carbon atoms, an acetyl group, and a diarylamino group of 6 to 24 carbon atoms. When a plurality of substituents are present, they may be identical with or different from one another. The number of carbon atoms in the substituents is included in counting the total number of carbon atoms in the aforementioned aromatic rings having substituents In general formula (1), Z is a group formed by removing one of Ars from a compound represented by formula (1a).

In formula (1a), ring A is a hydrocarbon ring represented by formula (1b) and fused to the adjacent rings and ring B is a heterocyclic ring represented by formula (1c) and fused to the adjacent rings. Although the hydrocarbon ring represented by formula (1b) may be fused to the adjacent rings at arbitrary positions, the number of positions where fusion can occur is structurally limited. That is, this hydrocarbon ring has 6 sides, but two adjacent sides in the ring cannot be fused respectively to the two adjacent rings. Likewise, the heterocyclic ring represented by formula (1c) may be fused to the adjacent rings at arbitrary positions, but here again the position where fusion can occur is structurally limited. This heterocyclic ring has five sides, but two adjacent sides cannot be fused respectively to the two adjacent rings nor the side containing N can be fused to the adjacent ring. Therefore, the number of skeletons of the compound represented by formula (1a) is limited, but this number increases as n increases.

In formula (1a), n is an integer of 2 to 4, preferably 2 or 3, more preferably 2. In this case, n number of ring As or ring Bs may be identical with or different from one another. Likewise, the positions of fusion of ring A to ring B may be identical with or different from one another.

In formulas (1a) and (1b), each R is independently a hydrogen atom, an aliphatic hydrocarbon group of 1 to 10 carbon atoms, an aromatic hydrocarbon group of 6 to 18 carbon atoms, or an aromatic heterocyclic group of 3 to 17 carbon atoms; preferably, a hydrogen atom, an aliphatic hydrocarbon group of 1 to 6 carbon atoms, a phenyl group, a pyridyl group, a pyrimidyl group, or a triazyl group; more preferably, a hydrogen atom, a phenyl group, a pyridyl group, a pyrimidyl group, or a triazyl group.

In formulas (1a) and (1c), each Ar is independently an aromatic hydrocarbon group of 6 to 50 carbon atoms or an aromatic heterocyclic group of 3 to 50 carbon atoms, preferably an aromatic hydrocarbon group of 6 to 18 carbon atoms, an aromatic heterocyclic group of 3 to 18 carbon atoms, or an aromatic compound in which a plurality of these aromatic rings are linked together. In the case where a plurality of aromatic rings are linked together, the total number of carbon atoms is 6 to 50. Specific examples of the aromatic hydrocarbon group or aromatic heterocyclic group are the same as those for of L where L is a monovalent group.

In formula (1), at least one of L and Ars is an m-valent or monovalent group derived from a compound represented by formula (1d). A plurality of Ars exist and, in the case where Ar is the aforementioned m-valent or monovalent group, it suffices if one of Ars is an m-valent or monovalent group.

In formula (1d), X is a methine group, a nitrogen atom, or C—Ar$_1$ and at least one of Xs is a nitrogen atom. In the case where L or Ar is an m-valent or monovalent group, the m number of methine groups or a methine group represent the m number of carbon atoms or a carbon atom remaining after removal of the m number of hydrogen atoms or a hydrogen atom.

In the case where X is a nitrogen atom in formula (1d), the total number of nitrogen atoms is preferably an integer of 1 to 4, more preferably an integer of 1 to 3. However, in the case where X is an m-valent group, m+number of nitrogen atoms is 6 or less.

In the case where X is C—Ar$_1$ in formula (1d), the total number of C—Ar$_1$s is preferably an integer of 1 to 3, more preferably 1 or 2.

In formula (1d), each Ar$_1$ is independently an aromatic hydrocarbon group of 6 to 50 carbon atoms or an aromatic heterocyclic group of 3 to 50 carbon atoms, preferably an aromatic hydrocarbon group of 6 to 18 carbon atoms, an aromatic heterocyclic group of 3 to 18 carbon atoms, or an aromatic compound in which a plurality of these aromatic rings are linked together. In the case where a plurality of aromatic rings are linked together, the total number of carbon atoms is 6 to 50. Specific examples of the aromatic hydrocarbon group or aromatic heterocyclic group are the same as those for of L where L is a monovalent group.

In general formula (1), m is an integer of 1 to 4, preferably an integer of 1 to 3, more preferably 1 or 2.

In the case where m is 2 or more in general formula (1), the numerical value of n and the positions of fusion of ring A to ring B may be identical in each case or differ from case to case.

The indolocarbazole compounds represented by general formula (1) can be synthesized by selecting raw materials according to the structure of the target compound and using a known technique.

For example, the diindolo[2,3-a:3',2'-i]carbazole skeleton (A), the diindolo[2,3-a:2',3'-h]carbazole skeleton (B), and the diindolo[3,2-b:2',3'-h]carbazole skeleton (C) can respectively be synthesized by the reaction formulas shown below with reference to synthetic examples described in The Journal of Organic Chemistry, 2004, Vol. 69 (17), 5705 and Organic Letters, 2004, Vol. 6, No. 19, 3413.

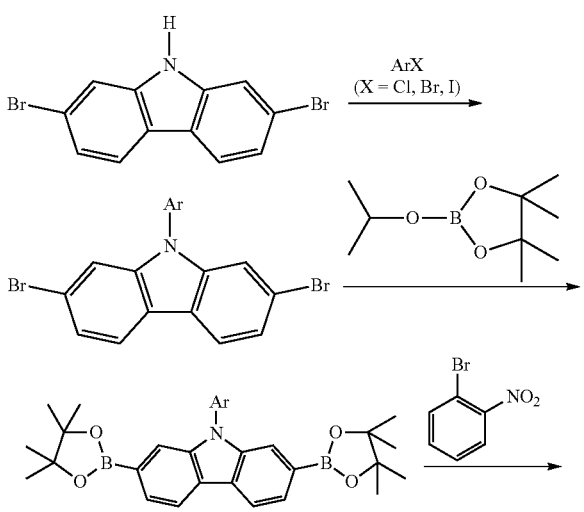

-continued

Diindolo[2,3-a:3',2'-i]carbazole skeleton (A)

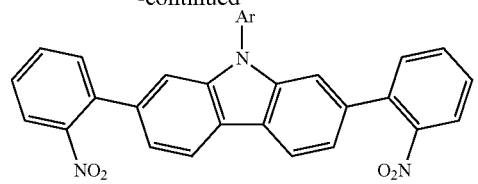

Diindolo[2,3-a:2',3'-h]carbazole skeleton (B)

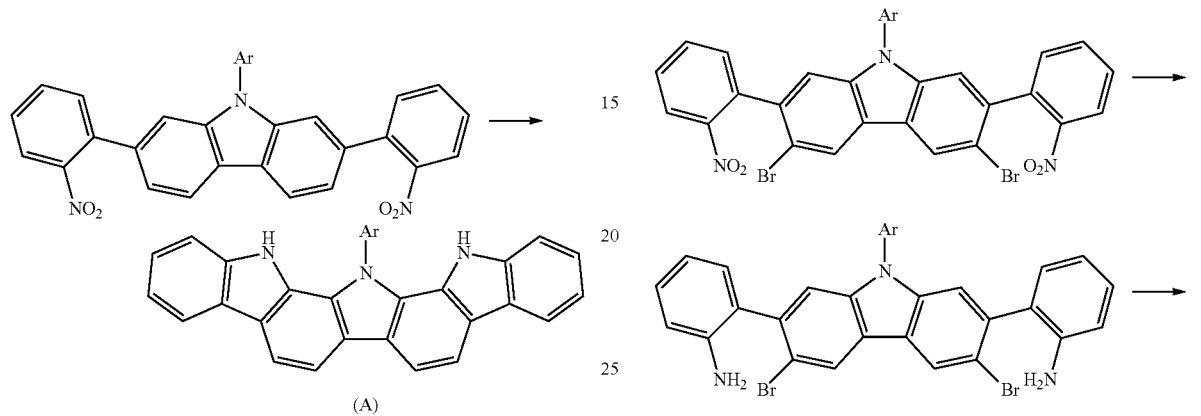

Diindolo[3,2-b:2',3'-h]carbazole skeleton (C)

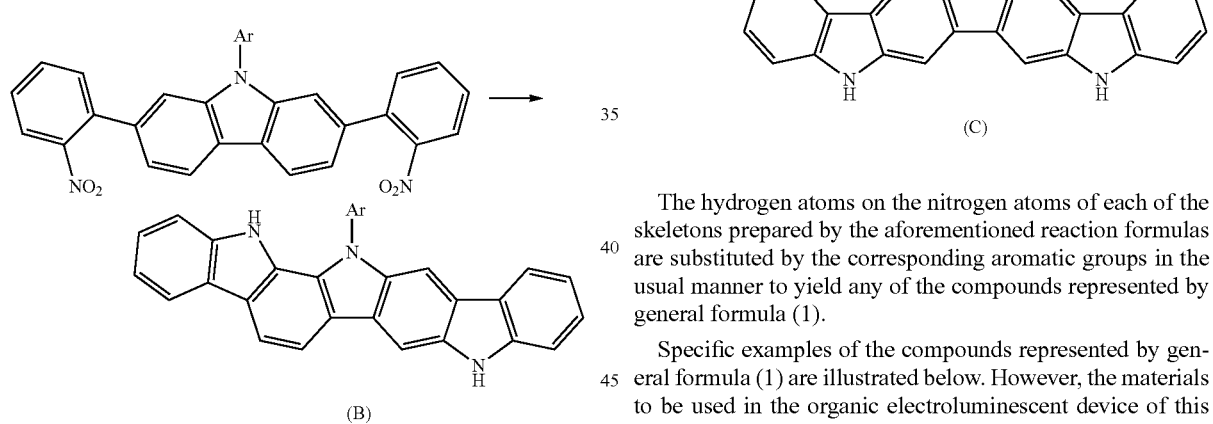

The hydrogen atoms on the nitrogen atoms of each of the skeletons prepared by the aforementioned reaction formulas are substituted by the corresponding aromatic groups in the usual manner to yield any of the compounds represented by general formula (1).

Specific examples of the compounds represented by general formula (1) are illustrated below. However, the materials to be used in the organic electroluminescent device of this invention are not limited thereto. The number assigned to the chemical formula denotes the compound number.

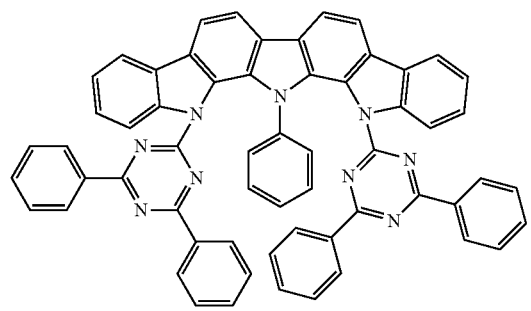

(1)

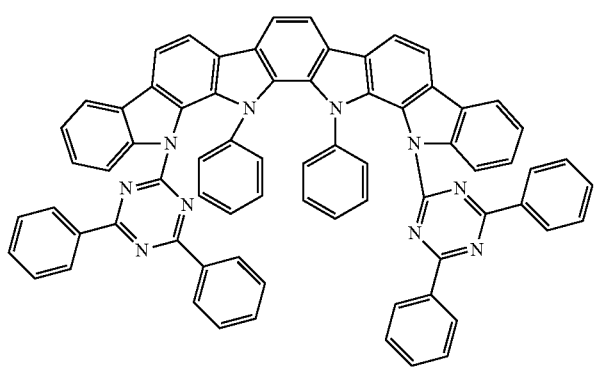

(2)

(3)
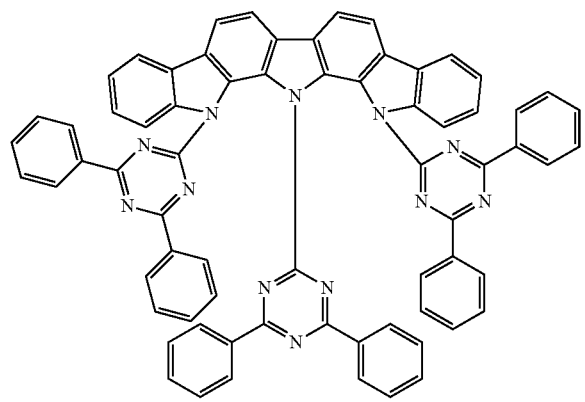
(4)
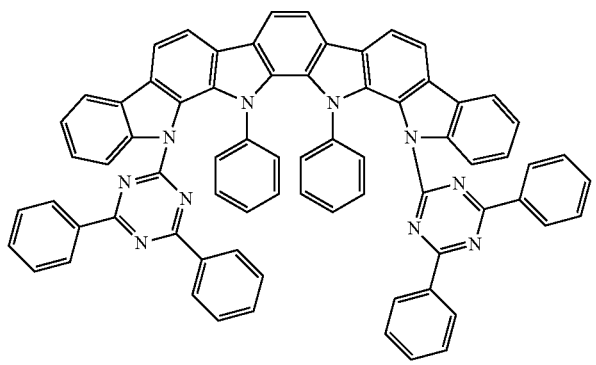
(5)
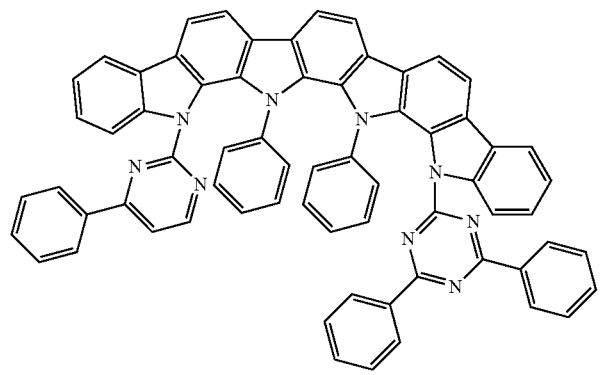
(6)
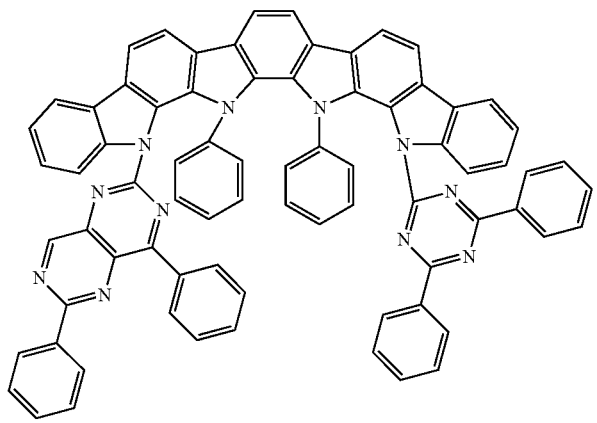
(7)
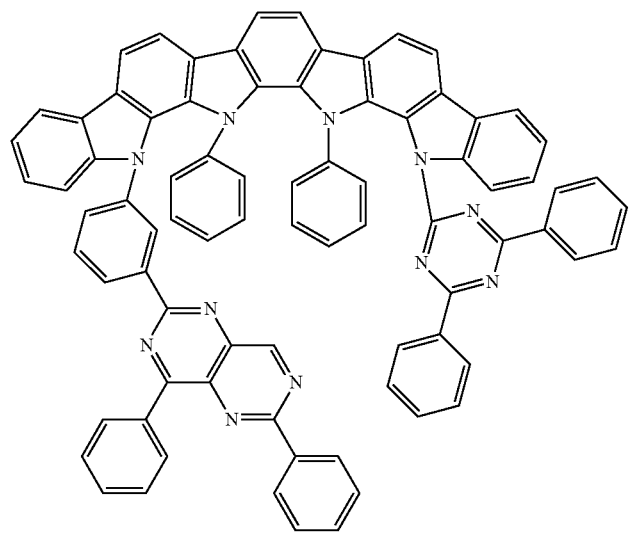

-continued
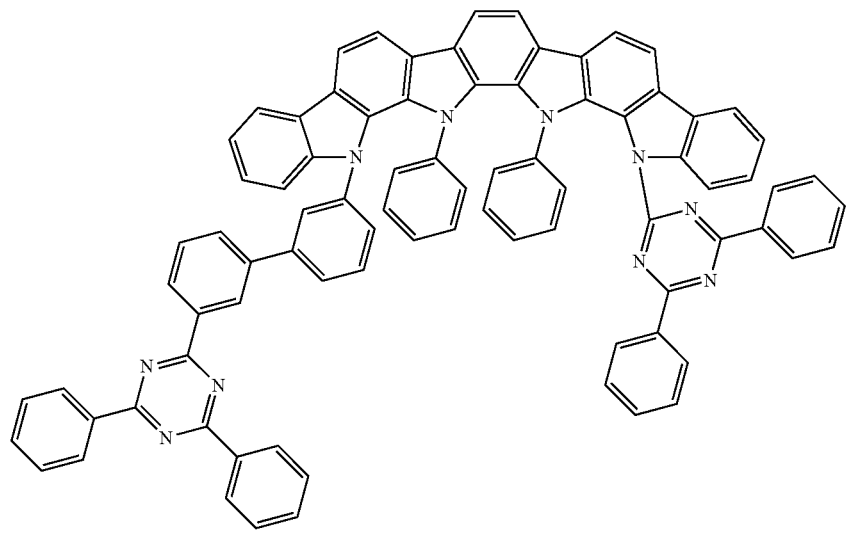
(8)
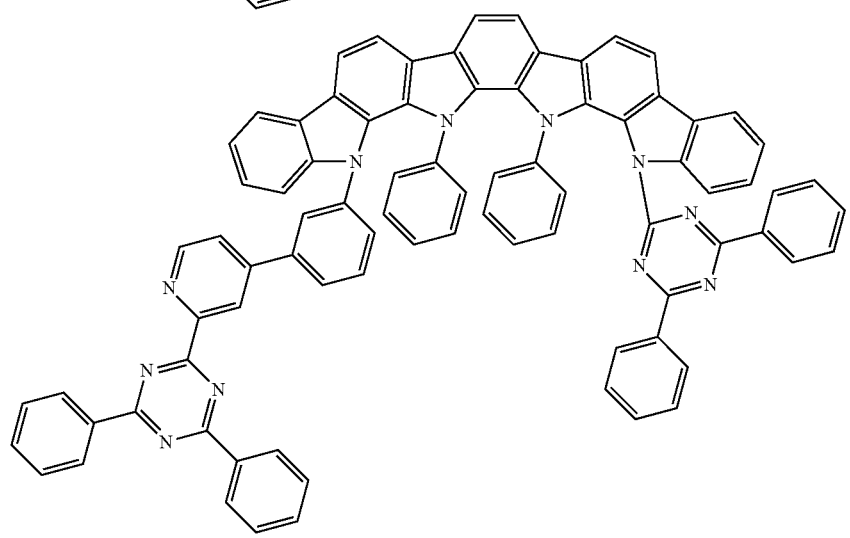
(9)
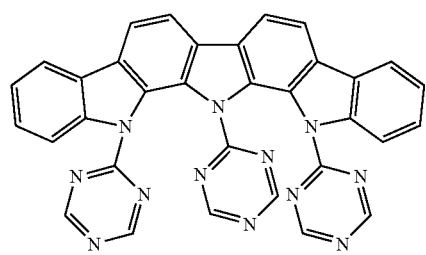
(10)
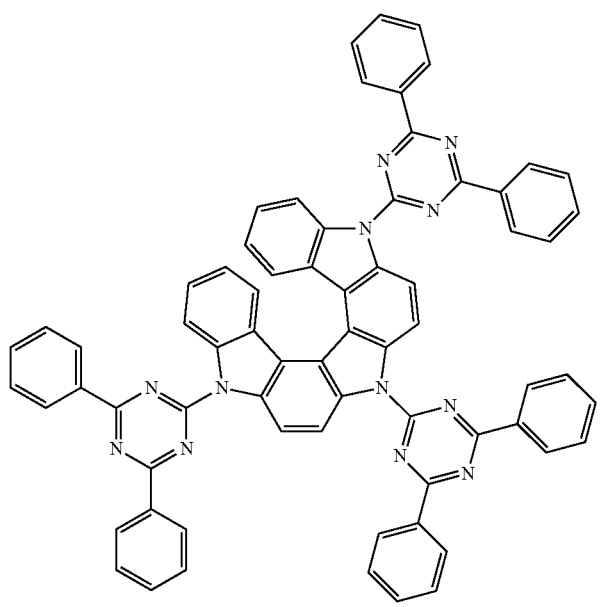
(11)

-continued
(12)
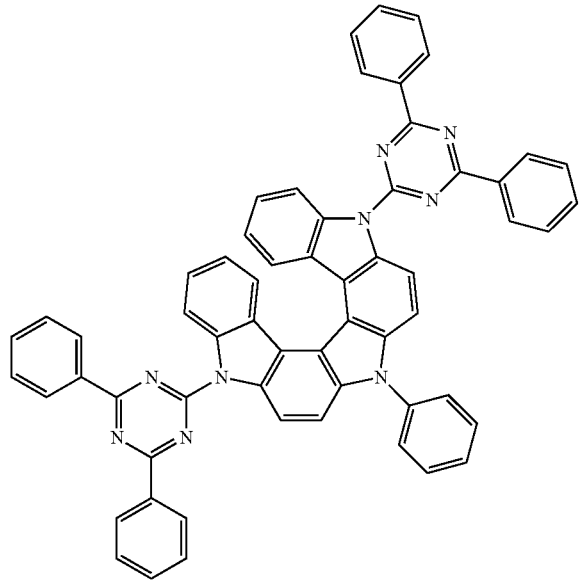
(13)
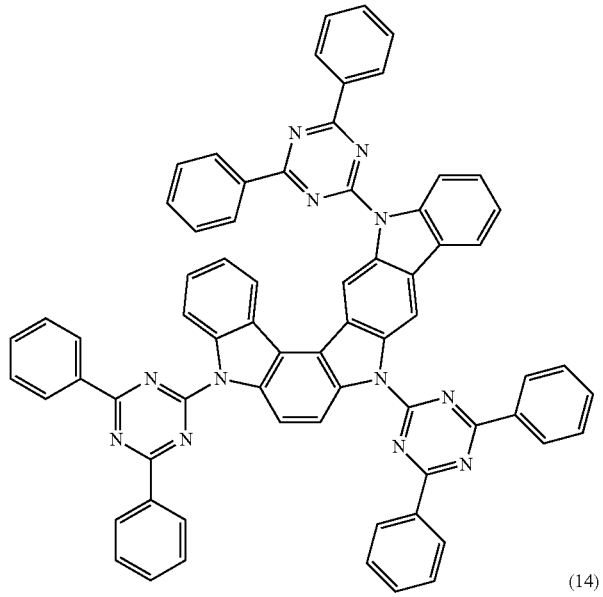
(14)
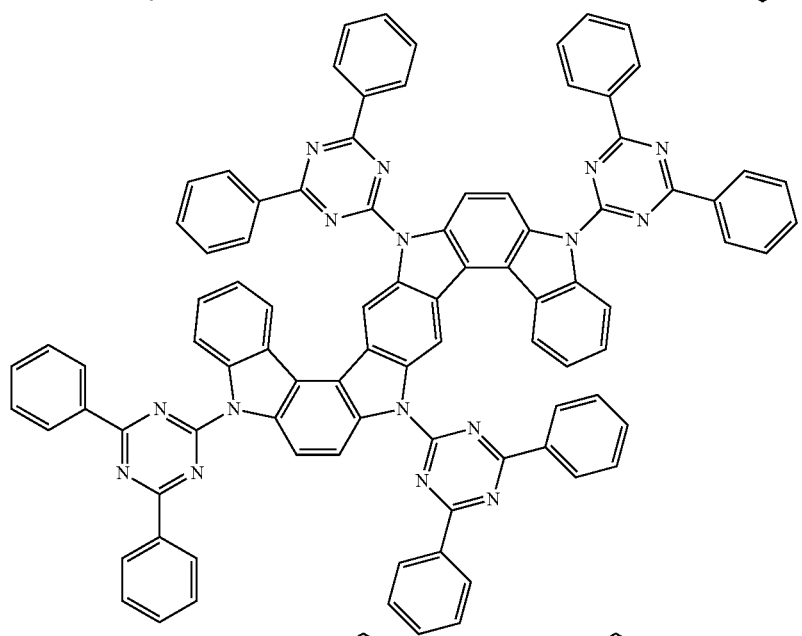
(15)
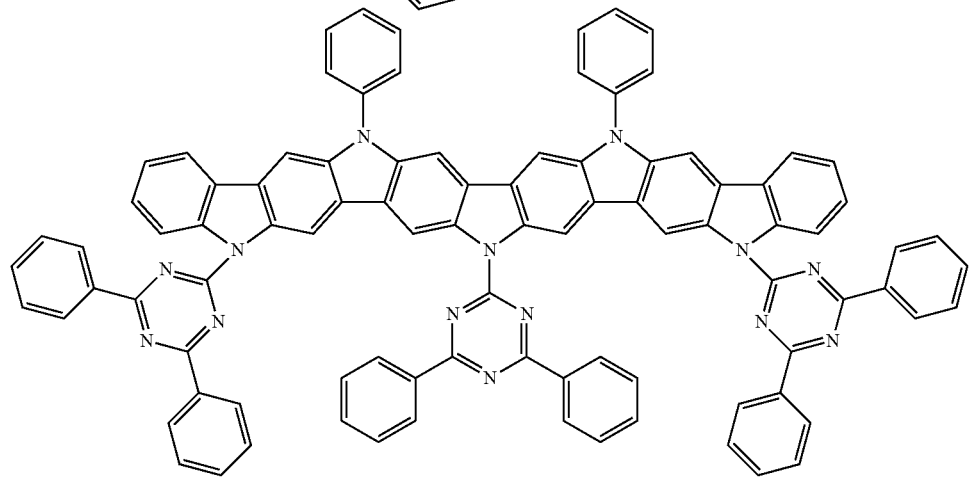

(16)
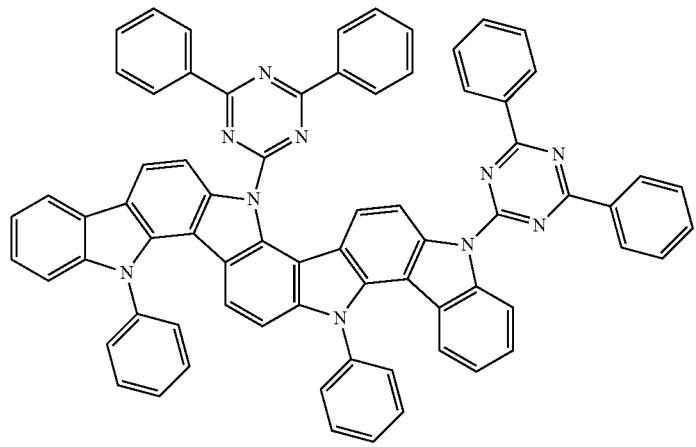
(17)
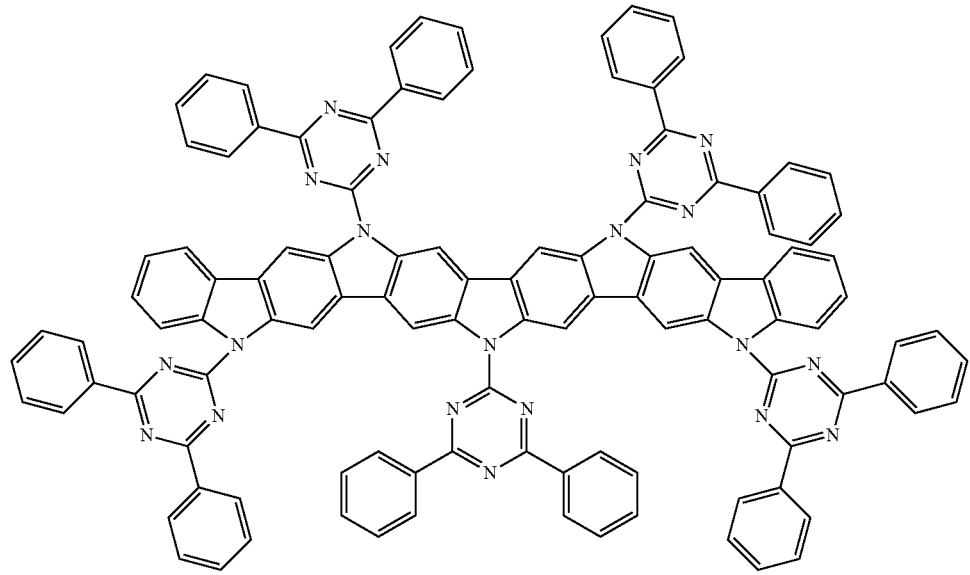
(18)
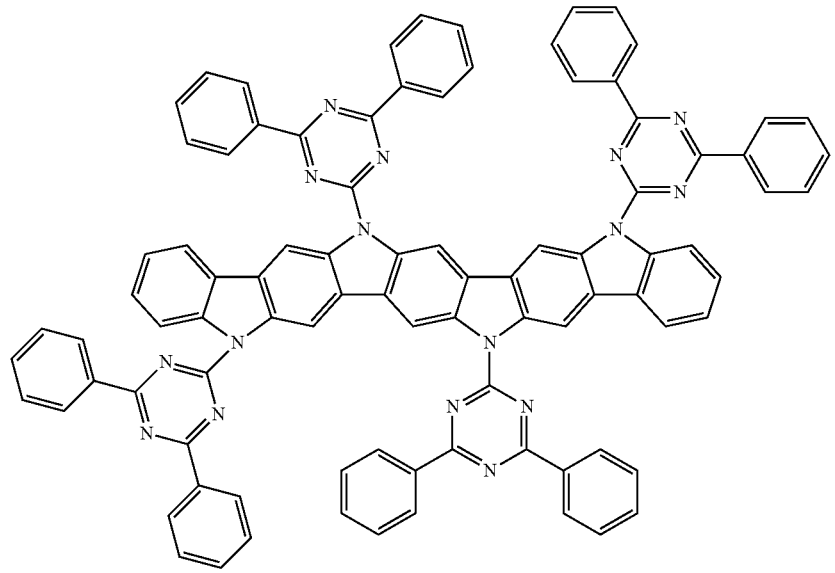

-continued
(19)
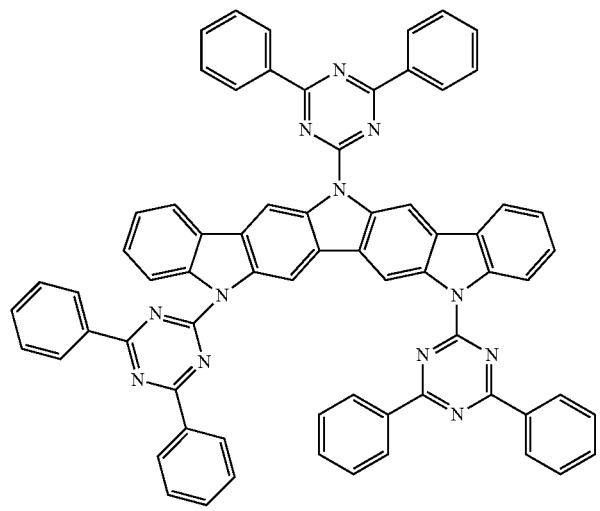
(20)
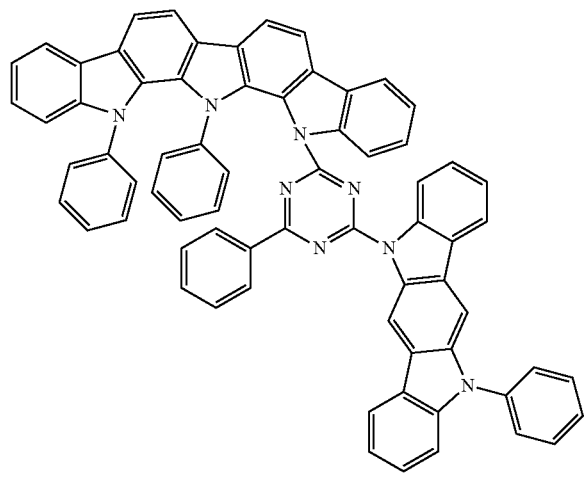
(21)
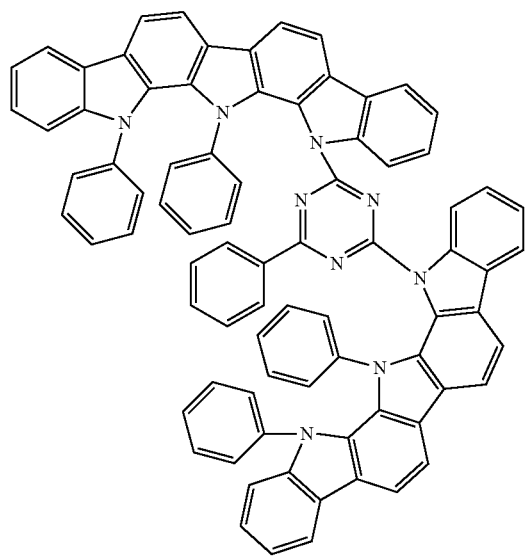
(22)
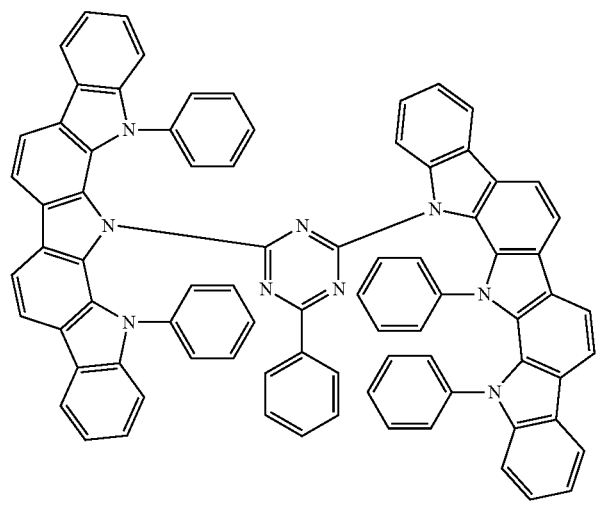
(23)
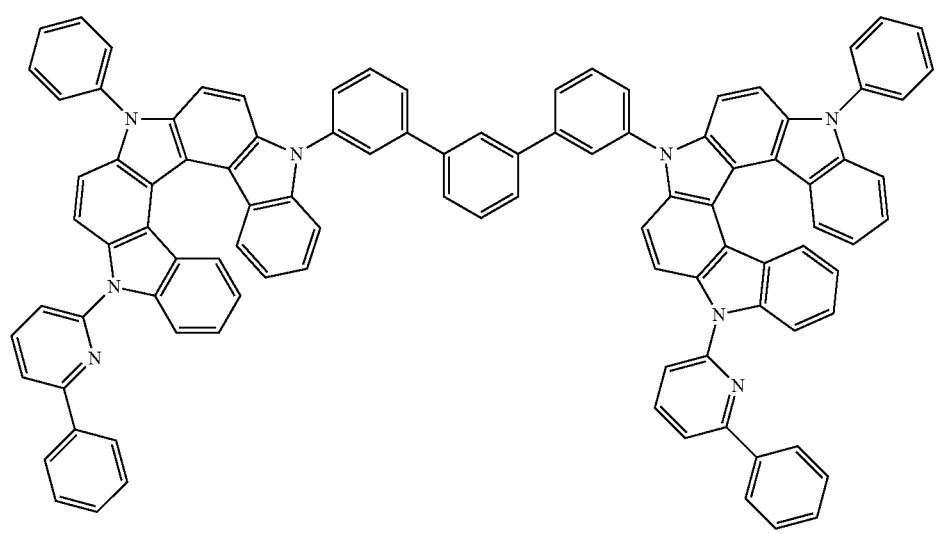

-continued
(24)
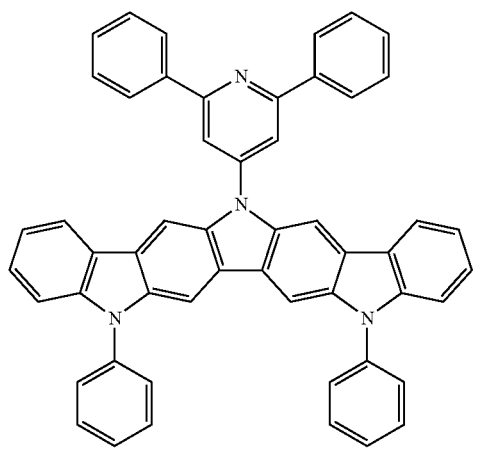
(25)
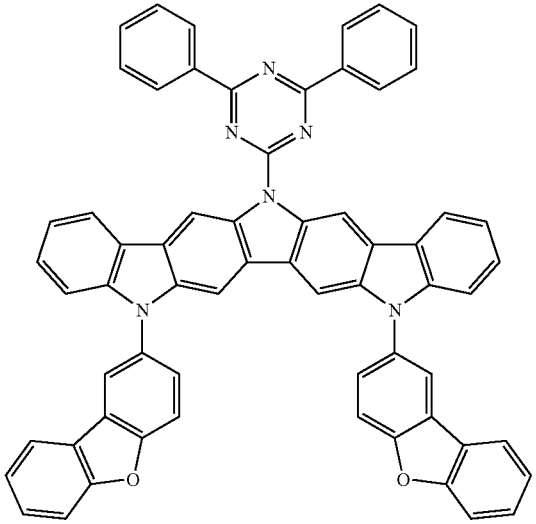
(26)
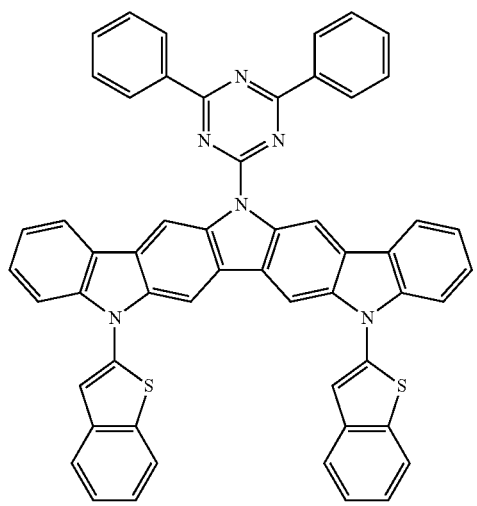
(27)
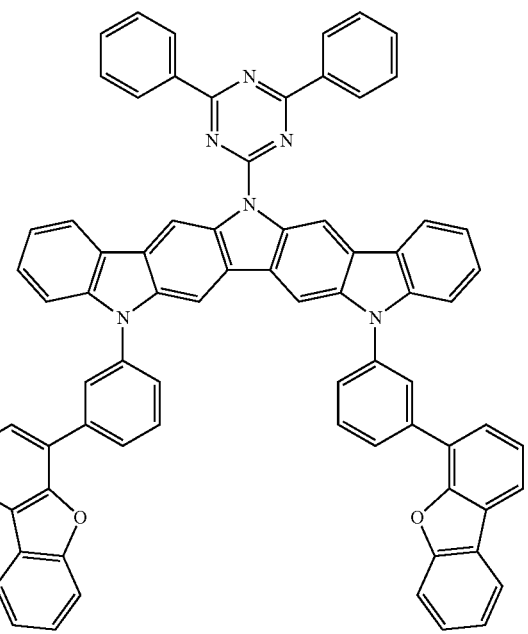
(28)
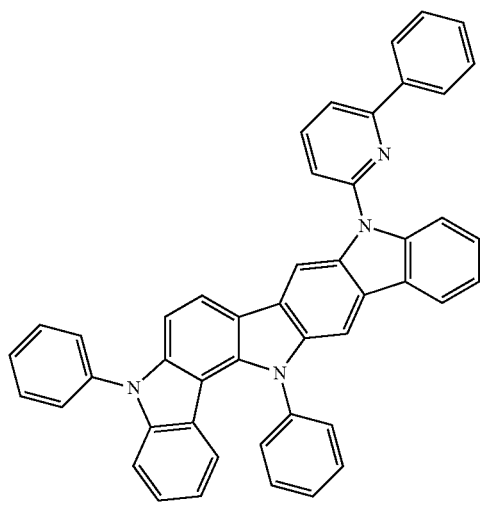
(29)
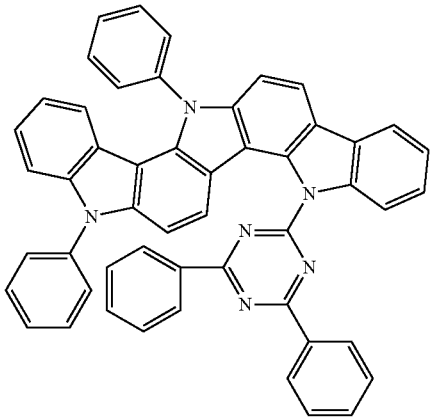

(30)
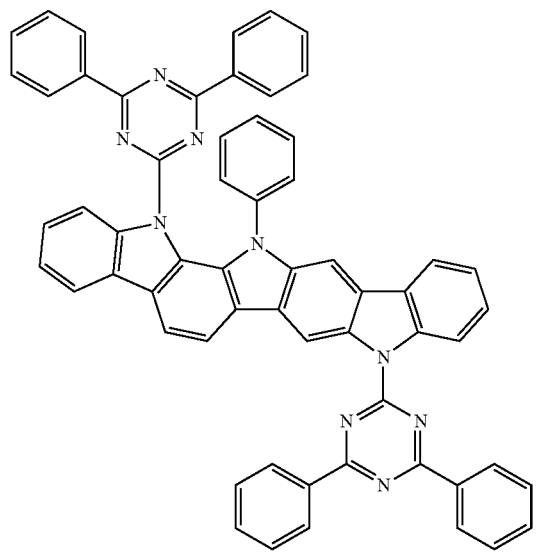
(31)
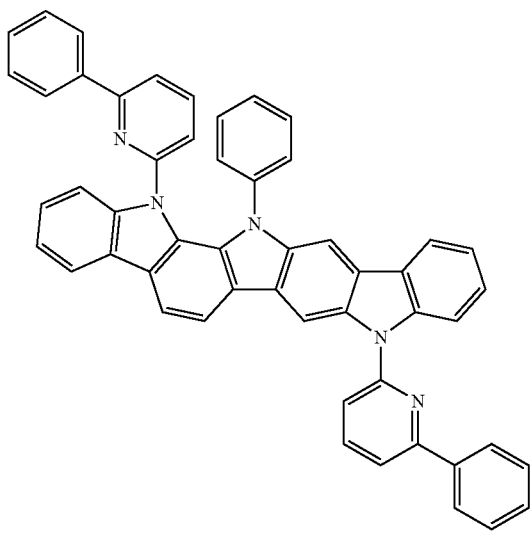
(32)
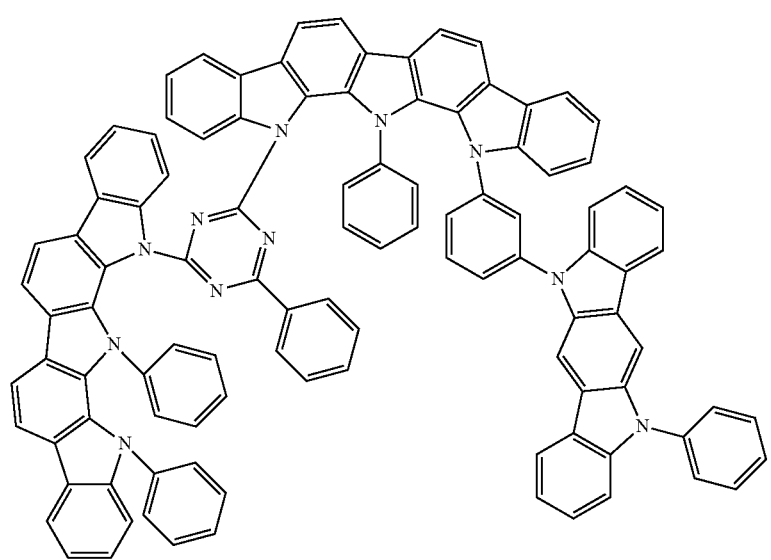

(33)
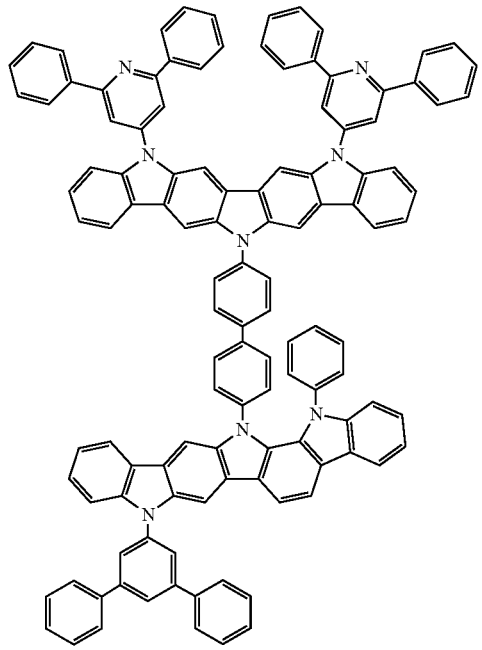
(34)
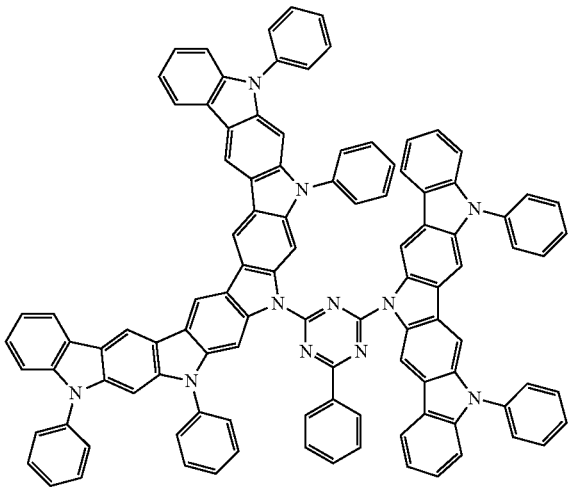
(35)
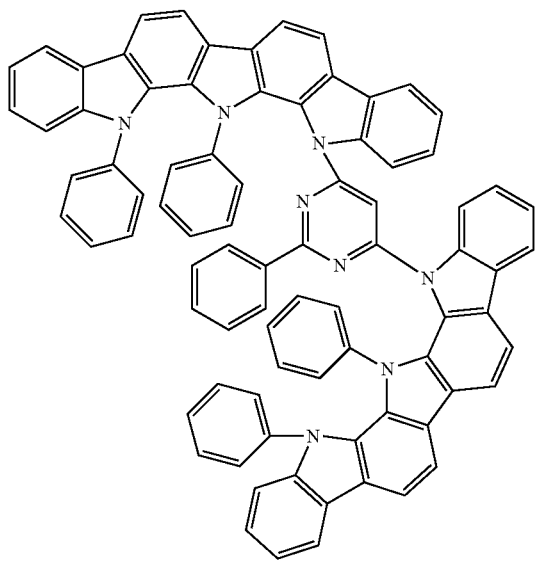
(36)
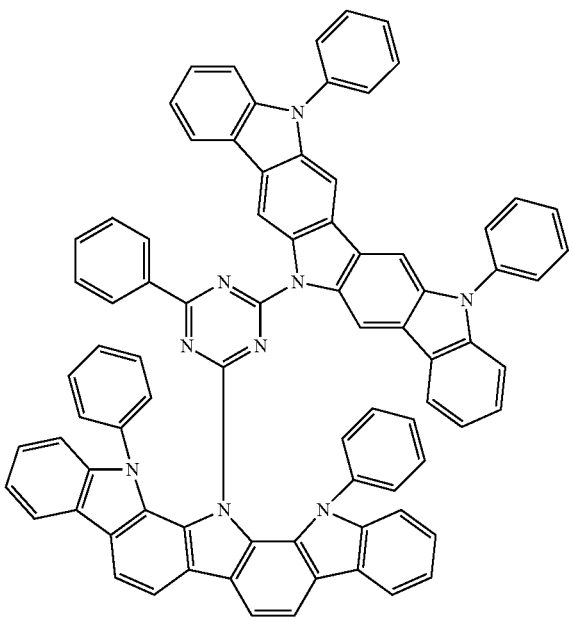

(37)

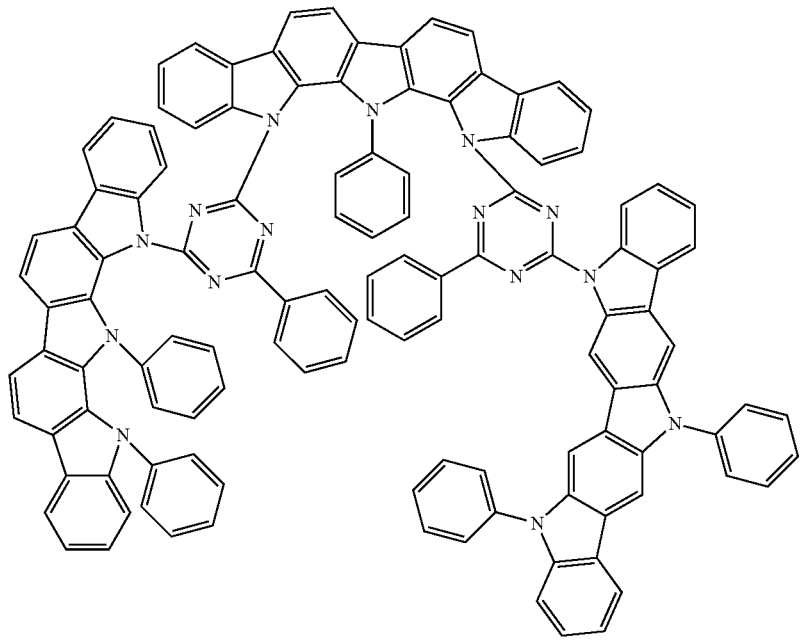

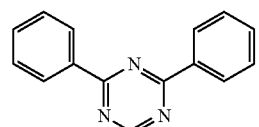

(38)

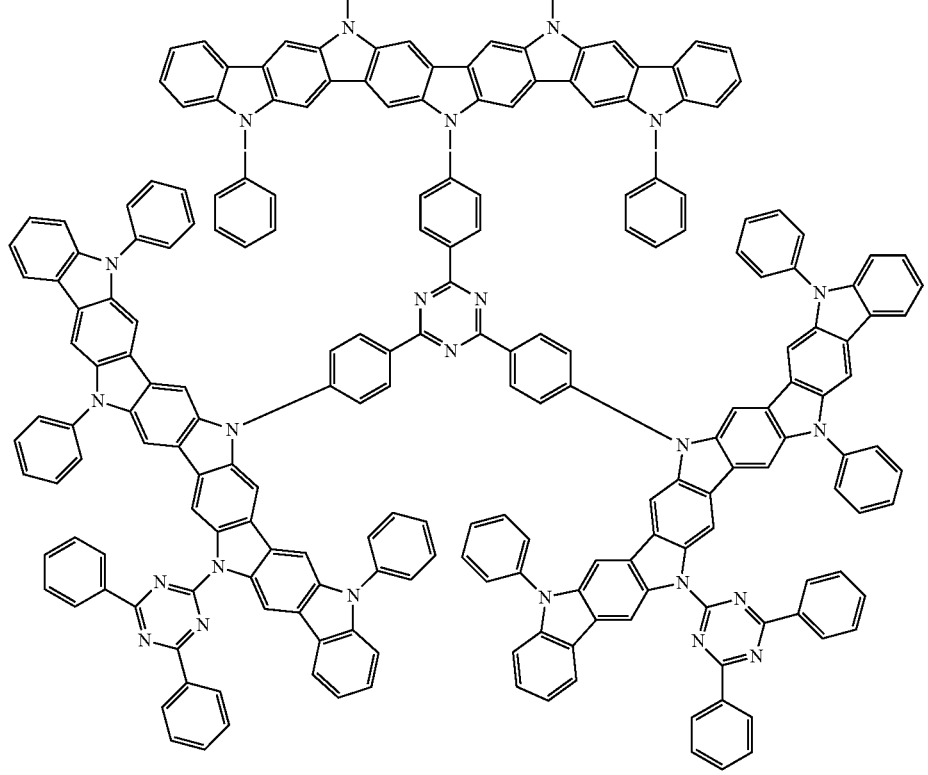

Provided that an organic EL device comprises an anode, a plurality of organic layers, and a cathode piled one upon another on a substrate, incorporation of a compound represented by general formula (1) in at least one of the organic layers helps provide an excellent organic EL device. An organic layer suitable for this purpose is a light-emitting layer, an electron-transporting layer, a hole-blocking layer, or an electron-blocking layer. Preferably, the compound is incorporated as a host material in a light-emitting layer containing a phosphorescent dopant.

An organic EL device according to this invention is explained hereinafter.

The organic EL device of this invention comprises organic layers at least one of which contains a light-emitting layer disposed between an anode and a cathode piled one upon another on a substrate and, further, at least one organic layer selected from a light-emitting layer, an electron-transporting layer, a hole-blocking layer, and an electron-blocking layer contains a compound represented by general formula (1). Advantageously, the light-emitting layer contains a compound represented by general formula (1) together with a phosphorescent dopant.

The structure of the organic EL device of this invention is explained hereinafter with reference to the drawing, but the structure is not limited to the one illustrated in the drawing.

FIG. 1 is the cross section to illustrate an example of the structure of an organic EL device generally used in this invention and the numbers in the FIGURE stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may further comprise an exciton-blocking layer adjacent to the light-emitting layer or an electron-blocking layer between the light-emitting layer and the hole-injecting layer. The exciton-blocking layer may be inserted either on the anode side or on the cathode side of the light-emitting layer or may be inserted simultaneously on both sides. The organic EL device of this invention comprises the substrate, the anode, the light-emitting layer, and the cathode as essential layers. However, it is preferable that the device comprises a hole-injecting/transporting layer and an electron-injecting/transporting layer in addition to the essential layers and further comprises a hole-blocking layer between the light-emitting layer and the electron-injecting/transporting layer. The hole-injecting/transporting layer means a hole-injecting layer and/or a hole-transporting layer while the electron-injecting/transporting layer means an electron-injecting layer and/or an electron-transporting layer.

The organic EL device of this invention can be so constructed as to have a structure that is the reverse of the structure illustrated in FIG. 1 by piling the cathode 7, the electron-transporting layer 6, the light-emitting layer 5, the hole-transporting layer 4, and the anode 2 one upon another in this order on the substrate 1. In this case, it is also possible to add or omit a layer or layers according to the need.

—Substrate—

The organic EL device of this invention is preferably supported by a substrate. There is no specific restriction on the substrate and any of the substrates which have been used customarily in organic EL devices can be used. For example, a substrate made from glass, transparent plastic, or quartz may be used.

—Anode—

The anode of an organic EL device is preferably made from an electrode substance having a high work function (4 eV or more) such as a metal, an alloy, an electrically conductive compound, and a mixture thereof. Specific examples of the electrode substances of this kind include metals such as Au and electrically conductive transparent materials such as CIA indium tin oxide (ITO), $SnO_2$, and ZnO. Further, a material that is amorphous and formable into a transparent electrically conductive film such as IDIXO ($In_2O_3$—ZnO) may be used. The anode may be formed by preparing a thin film from any of those electrode substances by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode substance. In the case where a substance that is applicable by a coating method such as an electrically conductive organic compound is used, a wet film-forming process such as printing and coating may be employed. When emitted light is taken out from the anode, the transmittance is desirably set at 10% or more and the sheet resistance as the anode is preferably several hundred Ω/□ or less. Further, the thickness of the film is normally selected from the range of 10 to 1,000 nm, preferably 10 to 200 nm, although it varies with the film-forming material.

—Cathode—

Meanwhile, the cathode is made from an electrode substance having a low work function (4 eV or less) such as a metal (hereinafter referred to as electron-injecting metal), an alloy, an electrically conductive compound, and a mixture thereof. Specific examples of the electrode substances of this kind include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. From the viewpoint of electron-injecting property and durability against oxidation and the like, a mixture of an electron-injecting metal and a second metal that is higher in work function and more stable than the electron-injecting metal is suitable for use as an electrode substance and examples thereof include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by preparing a thin film from any of those electrode substances by a method such as vapor deposition and sputtering. The sheet resistance as the cathode is preferably several hundred Ω/□ or less and the thickness of the film is selected from the range of 10 nm to 5 μm, preferably 50 to 200 nm. Making either the anode or the cathode of an organic EL device transparent or translucent in order to transmit emitted light advantageously improves the luminance.

A transparent or translucent cathode may be made by forming a cathode with a film thickness of 1 to 20 nm from the aforementioned metal and then forming thereon a film of one of the electrically conductive transparent materials described above in explanation of the anode. This method can be applied to fabricate a device in which both the anode and the cathode display good transmittance properties.

—Light-Emitting Layer—

The light-emitting layer is a phosphorescent light-emitting layer and contains a phosphorescent dopant and a host material. Examples of the phosphorescent dopant include an organic metal complex containing at least one metal selected from ruthenium, rhodium, palladium, silver, rhenium, osmium, iridium, platinum, and gold. The organic metal complexes of this kind are known in the aforementioned prior art technical documents and elsewhere and a suitable organic metal complex may be selected from them and used.

Preferable examples of the phosphorescent dopant include a complex containing a noble metal element such as Ir in the center, typically Ir(ppy)$_3$, a complex such as (Bt)$_2$Iracac, and a complex such as (Btp)Ptacac. Specific examples of these complexes are illustrated below, but the complexes useful for this invention are not limited thereto.

31
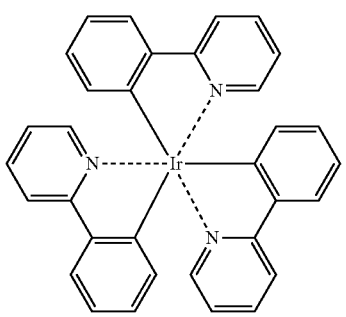
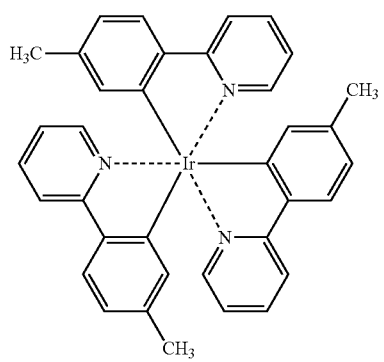
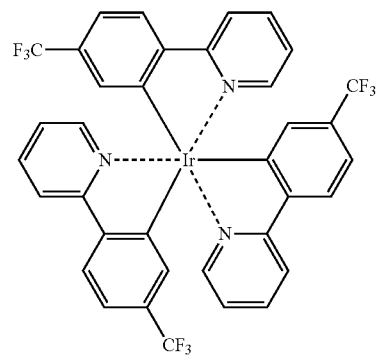
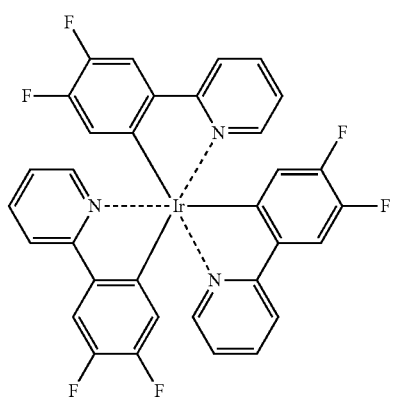
32
-continued
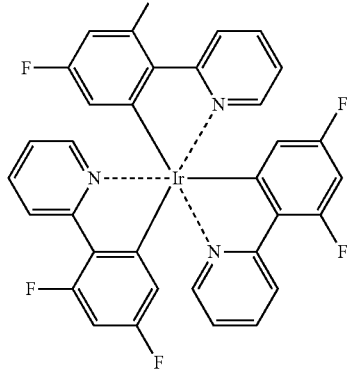
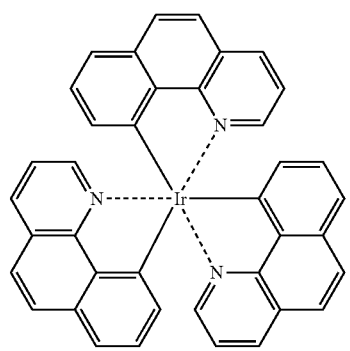
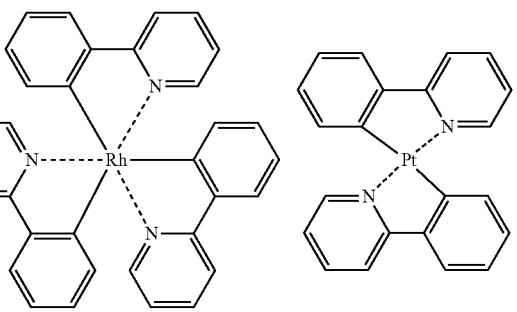
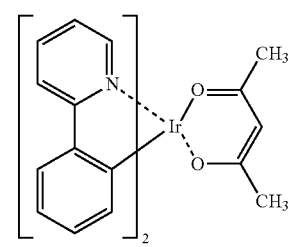
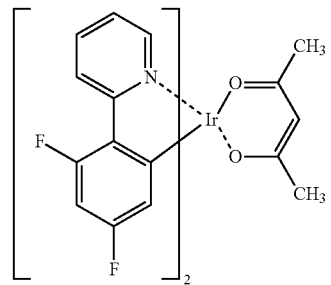

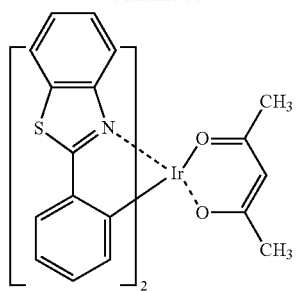
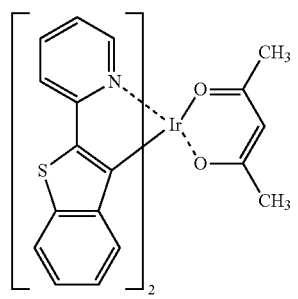
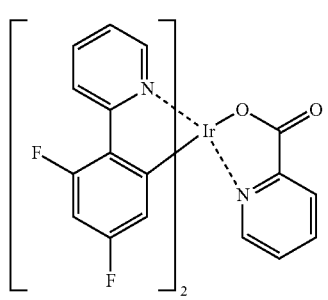
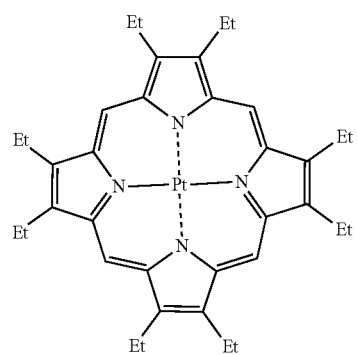
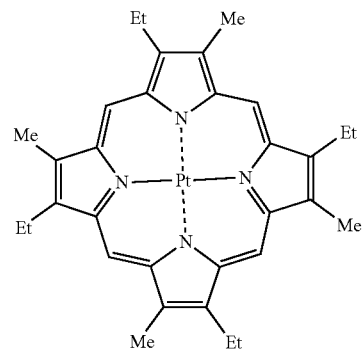
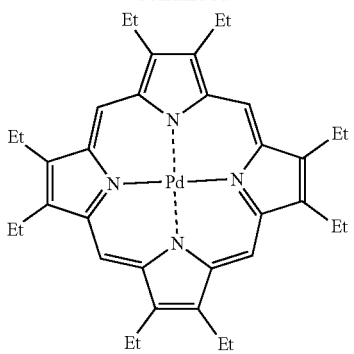
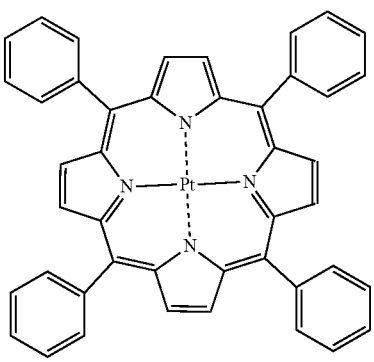
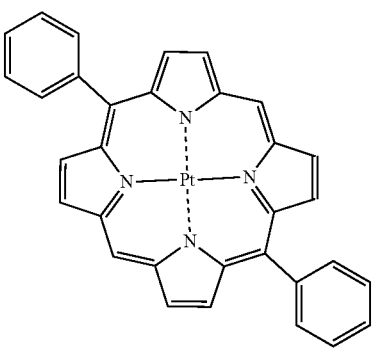
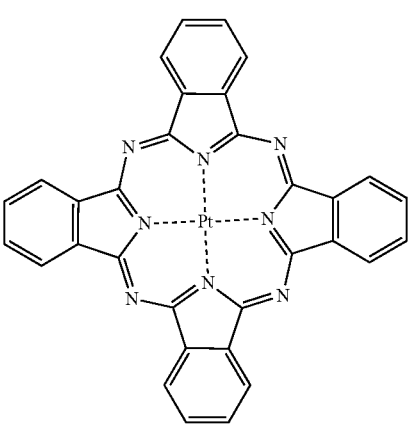

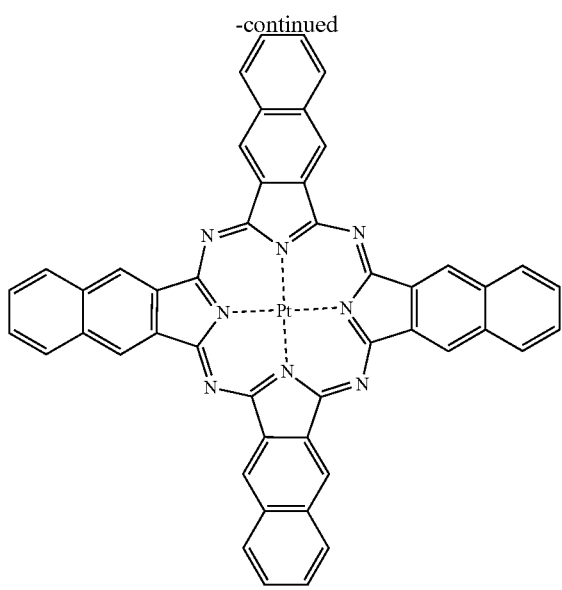

The content of the aforementioned phosphorescent dopant in the light-emitting layer is preferably in the range of 1 to 50 wt %, more preferably 5 to 30 wt %.

It is preferable to use a compound represented by the aforementioned general formula (1) as a host material in the light-emitting layer. However, in the case where the said compound is used in an organic layer other than the light-emitting layer, a host material other than the said compound may be used in the light-emitting layer. Further, the said compound may be used together with other host material. Still further, plural kinds of known host materials may be used together.

Among the known host compounds, the ones suitable for use preferably have a hole transport ability and an electron transport ability, can prevent the wavelength of emitted light from shifting to longer wavelengths, and have a high glass transition temperature.

Such known host materials are described in a large number of patent documents and elsewhere and a suitable material may be selected from them. Specific examples include, but are not limited to, indole derivatives, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes of benzoxazole derivatives and benzothiazole derivatives, and polymer compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives.

—Injecting Layer—

The injecting layer is a layer which is provided between an electrode and an organic layer to reduce the driving voltage and improve the luminance. The injecting layer includes a hole-injecting layer and an electron-injecting layer and may be provided respectively between the anode and the light-emitting layer or the hole-transporting layer and between the cathode and the light-emitting layer or the electron-transporting layer. The injecting layer may be provided according to the need.

—Hole-Blocking Layer—

The hole-blocking layer has a function of the electron-transporting layer in a broad sense and is composed of a hole-blocking material that has an extremely poor ability to transport holes while having a function of transporting electrons. The hole-blocking layer can improve the probability of recombination of electrons and holes by transporting electrons while blocking holes.

It is preferable to use a compound represented by general formula (1) in the hole-blocking layer. However, in the case where the said compound is used in any of other organic layers, a known hole-blocking material may be used instead. Further, any one of the materials for the electron-transporting layer to be described later on may be used as a hole-blocking material according to the need.

—Electron-Blocking Layer—

The electron-blocking layer is composed of a material that has an extremely poor ability to transport electrons while having a function of transporting holes and it can improve the probability of recombination of electrons and holes by transporting holes while blocking electrons.

It is preferable to use a compound represented by general formula (1) in the electron-blocking layer. However, in the case where the said compound is used in any of other organic layers, a known electron-blocking material may be used instead. As a material for the electron-blocking layer, any one of the materials for the hole-transporting layer to be described later on may be used according to the need. The thickness of the electron-blocking layer is preferably 3 to 100 nm, more preferably 5 to 30 nm.

—Exciton-Blocking Layer—

The exciton-blocking layer is a layer for blocking excitons that are generated by the recombination of holes and electrons in the light-emitting layer from diffusing to the charge-transporting layer. The insertion of this layer makes it possible to efficiently confine excitons in the light-emitting layer and enhance the luminous efficiency of the device. The exciton-blocking layer may be inserted either on the anode side or on the cathode side adjacent to the light-emitting layer or simultaneously on both the anode and the cathode sides.

Examples of a material for the exciton-blocking layer include 1,3-dicarbazolylbenzene (mCP) and bis(2-methyl-8-quinolinolato)-4-phenylphenolatoaluminum (III) (BAlq).

—Hole-Transporting Layer—

The hole-transporting layer is composed of a hole-transporting material that has a function of transporting holes and it may be provided in a single layer or a plurality of layers.

The hole-transporting material has either a property of injecting or transporting holes or a property of constituting a barrier to electrons and it may be either an organic substance or an inorganic substance. Although it is preferable to use a compound represented by general formula (1) in the hole-transporting layer, a suitable compound is selected from known compounds and used. Specific examples of known hole-transporting materials suitable for use include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electrically conductive oligomers, particularly thiophene oligomers. Preferable examples include porphyrin compounds, aromatic tertiary amine compounds, and styrylamine compounds and more preferable examples include aromatic tertiary amine compounds.

—Electron-Transporting Layer—

The electron-transporting layer is composed of a material that has a function of transporting electrons and may be provided in a single layer or a plurality of layers.

An electron-transporting material (serving also as a hole-blocking material in some cases) may be an arbitrary material so long as it has a function of transporting electrons that are injected from the cathode to the light-emitting layer. It is preferable to use a compound represented by general formula (1) in the electron-transporting layer, but an arbitrary material may be selected from the known compounds and used. Examples of such known compounds include nitro-substituted fluorene derivatives, diphenylquinone derivatives, thiopyran dioxide derivatives, carbodiimide, fluorenylidenemethane derivatives, anthraquinodimethan derivatives, anthrone derivatives, and oxadiazole derivatives. Further, thiadiazole derivatives that are derived from the aforementioned oxadiazole derivatives by substituting a sulfur atom for the oxygen atom of the oxadiazole ring and quinoxaline derivatives that have a quinoxaline ring known as an electron-withdrawing group may be used as electron-transporting materials. Further, polymer materials that contain any of these materials in the polymer chain or polymer materials whose backbone is constituted of any of these materials may be used.

EXAMPLES

This invention is explained in more detail hereinafter with reference to the examples. However, this invention is not limited to the examples and can be reduced to practice in various modes unless such a practice exceeds the gist of this invention.

Synthetic Example 1

Synthesis of Compound 1

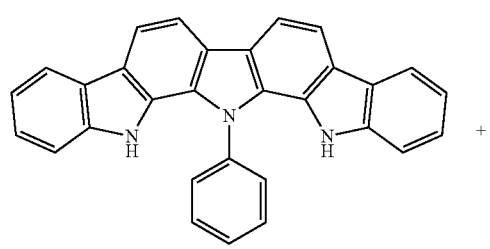

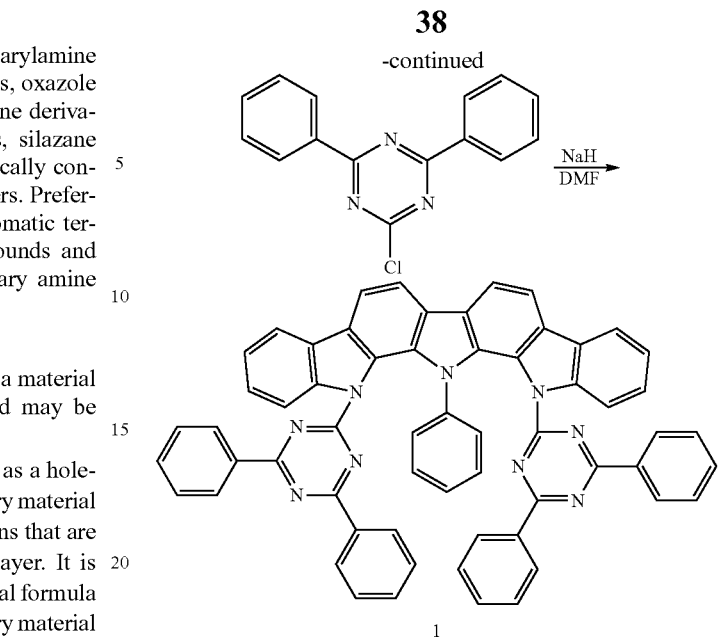

Under a nitrogen atmosphere, 100 ml of dehydrated N,N-dimethylformamide (DMF) was added to 2.52 g (0.059 mol) of sodium hydride (56.4% dispersion) and stirred. To 10.0 g (0.024 mol) of 5,7-dihydro-6-phenyl-diindolo[2,3-a:3',2'-i] carbazole was added 100 ml of DMF while allowing dissolution to occur and the resulting solution was added dropwise to the above mixture over 30 minutes. After completion of the dropwise addition, the stirring was continued at room temperature for 1 hour. Then, 100 ml of DMF was added to 13.97 g (0.052 mol) of 2-chloro-4,6-diphenyl-1,3,5-triazine while allowing dissolution to occur and the resulting solution was added dropwise to the above mixture over 30 minutes. After completion of the dropwise addition, the stirring was continued for 7 hours. Thereafter, the stirring was continued at 80° C. for 15 hours. The reaction mixture was cooled to room temperature, 300 ml of water was added, and the precipitated crystal was collected by filtration. The crystal was dried under reduced pressure, reslurried twice in methanol with application of heat, dried under reduced pressure, and purified by column chromatography to give 13.4 g (0.015 mol, 63% yield) of Compound 1.
APCI-TOFMS: m/z 884 [M+H]$^+$.

Further, Compounds 24, 22, 31, and 35 were prepared according to the methods described in the aforementioned Synthetic Example and in the specification and used in the fabrication of organic EL devices.

Example 1

The constituent layers were deposited in thin film by the vacuum deposition process at a degree of vacuum of $4.0\times10^{-5}$ Pa one upon another on a glass substrate on which a 110 nm-thick ITO anode had been formed. First, copper phthalocyanine (CuPC) was deposited on the ITO anode to a thickness of 25 nm. Then, 4,4'-bis[N-(1-naphthyl)-N-phenylamino]biphenyl (NPB) was deposited to a thickness of 40 nm to form a hole-transporting layer. Next, Compound 1 obtained in Synthetic Example 1 as a host material and tris (2-phenylpyridine)iridium (III) (Ir(ppy)$_3$) as a phosphorescent dopant were co-deposited on the hole-transporting layer from different deposition sources to a thickness of 40 nm to form a light-emitting layer. The concentration of Ir(ppy)$_3$ in the light-emitting layer was 10.0 wt %. Next, tris(8-hydroxyquinolinato)aluminum (III) (Alq3) was deposited to a thickness of 20 nm to form an electron-transporting layer. Further, lithium fluoride (LiF) was deposited on the electron-transporting layer to a thickness of 1.0 nm to form an electron-injecting layer. Finally, aluminum (Al) was deposited as an electrode on the electron-injecting layer to a thickness of 70 nm to finish the fabrication of an organic EL device.

Comparative Example 1

An organic EL device was fabricated as in Example 1 except that 4,4'-bis(9-carbazolyl)biphenyl (CBP) was used as the host material in the light-emitting layer.

Comparative Example 2

An organic EL device was fabricated as in Example 1 except that Compound H-1 shown below was used as the host material in the light-emitting layer.

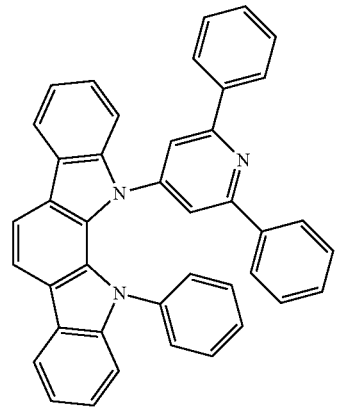

H-1

Each of the organic EL devices fabricated in Example 1 and Comparative Examples 1 and 2 was connected to an external power source and, when direct current voltage was applied, the device was confirmed to have the luminous characteristics shown in Table 1. In Table 1, the headword "compound" denotes the compound used as a host material and the values of the luminance, voltage, and luminous efficiency are obtained when the device was driven at 10 mA/cm$^2$. The peak emission wavelength of each device is 530 nm and this proves that light is emitted from Ir(ppy)$_3$.

TABLE 1

| | Compound | Luminance (cd/m$^2$) | Voltage (V) | Luminous efficiency (lm/W) |
|---|---|---|---|---|
| Example 1 | 1 | 2970 | 6.7 | 13.9 |
| Comparative Example 1 | CBP | 2420 | 9.3 | 8.2 |
| 2 | H-1 | 2840 | 7.4 | 12.1 |

Example 2

The constituent layers were deposited in thin film by the vacuum deposition process at a degree of vacuum of 4.0×10$^{-4}$ Pa one upon another on a glass substrate on which a 150 nm-thick ITO anode had been formed. First, copper phthalocyanine (CuPC) was deposited on the ITO anode to a thickness of 25 nm to form a hole-injecting layer. Then, NPB was deposited on the hole-injecting layer to a thickness of 55 nm to form a hole-transporting layer. Next, Compound 24 as a host material and bis(2-(2'-benzo[4,5-a]thienyl)pyridinato-N,C3]iridium(acetylacetonate) ((Btp)$_2$Iracac) were co-deposited on the hole-transporting layer from different deposition sources to a thickness of 47.5 nm to form a light-emitting layer. At this time, the concentration of (Btp)$_2$Iracac was 8.0 wt %. Next, Alq3 was deposited to a thickness of 30 nm to form an electron-transporting layer. Further, LiF was deposited on the electron-transporting layer to a thickness of 1 nm to form an electron-injecting layer. Finally, Al was deposited as an electrode on the electron-injecting layer to a thickness of 200 nm to finish the fabrication of an organic EL device.

Example 3

An organic EL device was fabricated as in Example 2 except that Compound 31 was used as the host material in the light-emitting layer.

Comparative Example 3

An organic EL device was fabricated as in Example 2 except that bis(2-methyl-8-quinolinolato)-4-phenylphenolatoaluminum (III) (BAlq) was used as the host material in the light-emitting layer.

Comparative Example 4

An organic EL device was fabricated as in Example 2 except that Compound H-1 was used as the host material in the light-emitting layer.

Each of the organic EL devices fabricated in Examples 2 and 3 and Comparative Examples 3 and 4 was connected to an external power source and, when direct current voltage was applied, the device was confirmed to have the luminous characteristics shown in Table 2. In Table 2, the values of the luminance, voltage, and luminous efficiency are obtained when the device was driven at 10 mA/cm$^2$. The peak emission wavelength of each device is 620 nm and this proves that light is emitted from (Btp)$_2$Iracac.

TABLE 2

| | Compound | Luminance (cd/m$^2$) | Voltage (V) | Luminous efficiency (lm/W) |
|---|---|---|---|---|
| Example 2 | 24 | 1410 | 6.6 | 6.7 |
| 3 | 31 | 1440 | 6.8 | 6.6 |
| Comparative Example 3 | BAlq | 1020 | 8.4 | 3.8 |
| 4 | H-1 | 1280 | 7.2 | 5.6 |

Example 4

An organic EL device having a structure formed by omitting the hole-transporting layer from and adding an electron-injecting layer to the structure shown in FIG. 1 was fabricated. A glass substrate on which a 150 nm-thick ITO anode had been formed was submitted to UV ozone cleaning and drying. A 20 wt % ethanol solution of PEDOT•PSS (Baytron P CH8000) was applied to the ITO anode on the glass substrate by spin coating at 3,000 rpm for 60 seconds and dried at 200° C. for 60 minutes to form a hole-injecting layer. At this time, the thickness of the hole-injecting layer was 25 nm. Then, a mixed solution of Compound 22 (38.0 parts by weight) as a host material and Ir(ppy)$_3$ (2.0 parts by weight) as a phosphorescent dopant in dichloromethane (2,840 parts by weight) was applied by spin coating at 4,000 rpm for 30 seconds and dried at 120° C. for 30 minutes to form a light-emitting layer. At this time, the thickness of the light-emitting layer was 70 nm. Then, Alq3 was vacuum-deposited at a rate of 0.1 nm/sec to a thickness of 35 nm to form an electron-transporting layer. Further, LiF was vacuum-deposited to a thickness of 0.5 nm to form an electron-injecting layer. Finally, Al as an electrode was vacuum-deposited to a thickness of 170 nm to finish the fabrication of an organic EL device.

Example 5

An organic EL device was fabricated as in Example 3 except that Compound 35 was used as the host material in the light-emitting layer.

Comparative Example 5

An organic EL device was fabricated as in Example 3 except that Compound H-1 was used as the host material in the light-emitting layer.

As the initial characteristics of the organic EL devices fabricated in Example 4 and Comparative Examples 5 and 6, the current efficiency (cd/A) was measured by connecting each device to an external power source and applying direct current voltage so as to generate an electric current at 100 mA/cm$^2$. The results are shown in Table 3.

TABLE 3

| | Compound | Current efficiency (cd/A) |
|---|---|---|
| Example 4 | 22 | 6.2 |
| 5 | 35 | 6.5 |
| Comparative Example 5 | H-1 | 5.6 |

INDUSTRIAL APPLICABILITY

The organic EL device of this invention satisfies a level of performance required for practical use with respect to the luminous characteristics, driving life, and durability and is of high technical value because of its potential applicability to flat panel displays (cellular phone display devices, vehicle-mounted display devices, office computer display devices, and television sets), light sources utilizing the characteristics of planar light emitters (illumination, light sources for copying machines, and backlight sources for liquid crystal displays and meters), display boards, and marker lamps.

The invention claimed is:

1. An organic electroluminescent device comprising an anode, organic layers containing a phosphorescent light-emitting layer, and a cathode piled one upon another on a substrate wherein at least one organic layer selected from the group consisting of a light-emitting layer, a hole-transporting layer, an electron-transporting layer, a hole-blocking layer, and an electron-blocking layer contains a compound represented by general formula (1);

$$(Z \!\!\!+\!\!\!)_m L \quad (1)$$

in general formula (1), Z is a group formed by removing one of Ars from a compound represented by formula (1a); L is an m-valent aromatic hydrocarbon group of 6 to 50 carbon atoms or an m-valent aromatic heterocyclic group of 3 to 50 carbon atoms; m is an integer of 1 to 4 and, when m is 2 or more, Zs may be identical with or different from one another;

in formula (1a), ring A is a hydrocarbon ring represented by formula (1b) and fused to the adjacent rings at arbitrary positions, ring B is a heterocyclic ring represented by formula (1c) and fused to the adjacent rings at arbitrary positions, and n is an integer of 2 to 4; in formulas (1a) and (1b), each R is independently a hydrogen atom, an aliphatic hydrocarbon group of 1 to 10 carbon atoms, an aromatic hydrocarbon group of 6 to 18 carbon atoms, or an aromatic heterocyclic group of 3 to 17 carbon atoms; and in formulas (1a) and (1c), each Ar is independently an aromatic hydrocarbon group of 6 to 50 carbon atoms or an aromatic heterocyclic group of 3 to 50 carbon atoms; however, at least one of L and Ars is an m-valent or monovalent group formed from a compound represented by formula (1d) by removing hydrogen atoms or a hydrogen atom;

in formula (1d), X is a methine group, a nitrogen atom, or C—Ar$_1$ and at least one of Xs is a nitrogen atom; each Ar$_1$ is independently an aromatic hydrocarbon group of 6 to 50 carbon atoms or an aromatic heterocyclic group of 3 to 50 carbon atoms.

2. An organic electroluminescent device as described in claim 1 wherein, in general formula (1), m is 1 or 2.

3. An organic electroluminescent device as described in claim 1 wherein, in general formula (1), n is 2.

4. An organic electroluminescent device as described in claim 2 wherein, in general formula (1), formula (1a) is represented by any one of the following formulas (2) to (4);

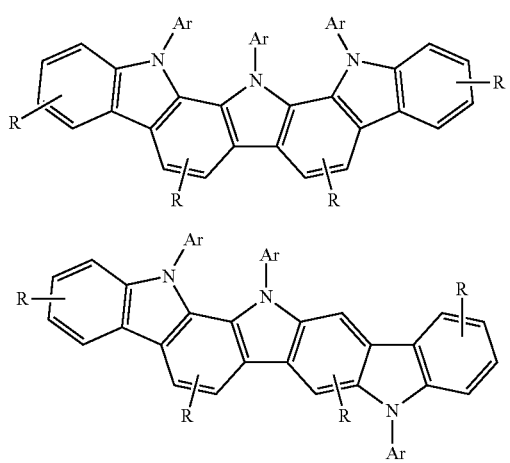
(2)
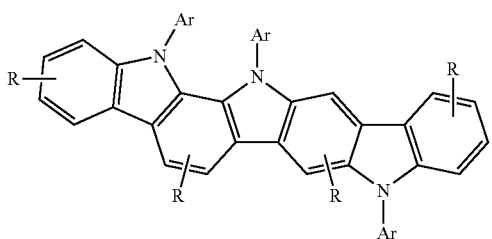
(3)
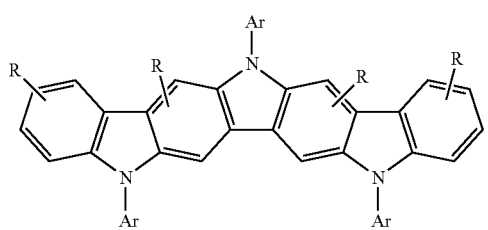
(4)
in formulas (2) to (4), Ar and R respectively have the same meaning as those in formulas (1a), (1b), and (1c).
5. An organic electroluminescent device as described in claim 1 wherein the organic layer containing a compound represented by general formula (1) is a light-emitting layer containing a phosphorescent dopant.
* * * * *